US009307990B2

(12) United States Patent
Filips et al.

(10) Patent No.: US 9,307,990 B2
(45) Date of Patent: Apr. 12, 2016

(54) WOUND CLAMP (75) Inventors: Dennis Frank Filips, Edmonton (CA); Ian Joseph Atkinson, Edmonton (CA)

(73) Assignee: Innovative Trauma Care, Inc., Edmonton (CA)

( * ) Notice: Subject to any disclaimer, the term of this patent is extended or adjusted under 35 U.S.C. 154(b) by 285 days.

(21) Appl. No.: 13/877,897

(22) PCT Filed: Oct. 19, 2011

(86) PCT No.: PCT/CA2011/001170
§ 371 (c)(1),
(2), (4) Date: Apr. 24, 2013

(87) PCT Pub. No.: WO2012/051706
PCT Pub. Date: Apr. 26, 2012

(65) Prior Publication Data
US 2013/0204294 A1 Aug. 8, 2013

Related U.S. Application Data (60) Provisional application No. 61/394,566, filed on Oct. 19, 2010.

(51) Int. Cl.
*A61B 17/08* (2006.01)
*A61B 17/064* (2006.01)
*A61B 17/28* (2006.01)

(52) U.S. Cl.
CPC .............. *A61B 17/08* (2013.01); *A61B 17/064* (2013.01); *A61B 2017/081* (2013.01); *A61B 2017/2837* (2013.01)

(58) Field of Classification Search
CPC .. A61B 17/08; A61B 17/083; A61B 17/0644; A61B 2017/081; A61B 2017/267; A61M 2025/024; A61M 2025/0286; Y10T 24/4453; Y10T 24/44538
USPC .......... 606/213–221; 70/17, 19, 159, 220, 16; 132/277, 279, 282–284; 403/91, 100, 403/105, 113; 294/28, 106, 209, 99.2; 24/545–547
See application file for complete search history.

(56) References Cited

U.S. PATENT DOCUMENTS 2,881,762 A * 4/1959 Lowrie ........................... 29/564
3,068,869 A * 12/1962 Shelden et al. ............... 606/216
4,317,451 A * 3/1982 Cerwin et al. ................ 606/220

(Continued)

FOREIGN PATENT DOCUMENTS

GB           456458      11/1936
SU         1301387 A      4/1987
WO    WO 2012/051706     4/2012

OTHER PUBLICATIONS

International Search Report regarding PCT/IB2013/003178.
(Continued)

*Primary Examiner* — Todd E Manahan
*Assistant Examiner* — Majid Jamialahmadi
(74) *Attorney, Agent, or Firm* — DLA Piper LLP (US)

(57) ABSTRACT

A wound closure device includes first and second opposing members which open and close in a clam-shell configuration, skin penetrating needles and a pressure bar for applying pressure to close the wound when the device is closed, and releasable locking means for biasing or maintaining the device in a closed position.

8 Claims, 10 Drawing Sheets

(56) References Cited

U.S. PATENT DOCUMENTS

| | | |
|---|---|---|
| 5,486,196 A | 1/1996 | Hirshowitz et al. |
| 2005/0251204 A1 * | 11/2005 | Attinger et al. ............... 606/221 |
| 2006/0167458 A1 | 7/2006 | Gabele |

OTHER PUBLICATIONS

Russian Office Action (with English translation) issued on May 7, 2015 regarding patent application No. RU 2013122861/14.

* cited by examiner

WOUND CLAMP

CROSS-REFERENCE TO RELATED APPLICATIONS

This application is a 35 USC §371 National Stage application of International Application No. PCT/CA2011/001170 filed Oct. 19, 2011, now pending; which claims the benefit under 35 USC §119(e) to U.S. Application Ser. No. 61/394,566 filed Oct. 19, 2010, now expired. The disclosure of each of the prior applications is considered part of and is incorporated by reference in the disclosure of this application.

FIELD OF THE INVENTION

The present invention relates to a clamp device for wound closure. In particular, the invention relates to a haemorrhage control device for closing a wound, particularly in emergency situations, such as during military operations or civilian disaster situations.

BACKGROUND

In both military and non-military emergency medical situations, it is often necessary to temporarily close a wound to prevent bleeding and to avoid contaminating the wound. In many situations, it is impractical to suture or staple a wound closed, which will often take five to ten minutes.

While utilization of strap style tourniquets have been widely accepted for field care, these devices present a number of disadvantages. Tourniquets are slow and difficult to maneuver and place around the extremity. They are limited by how high they can be placed on a limb and do not address major bleeding in the groin or axilla where larger blood vessels run or other areas of the body, such as the trunk, neck, or scalp. They create a lot of pain for the casualty and there is a risk of limb loss when left on too long. Pneumatic tourniquets are less painful but share all of the anatomical restrictions and are less sturdy for military field use.

As an alternative to manual pressure and packing with gauze, hemostatic agents and dressings have been developed to accelerate the clotting process in wounds. One such product, referred to as QuickClot™ (Z-Medica) comprises granular zeolites which are applied to the injured vessel, causing water absorption from the blood to the zeolite to concentrate clotting factors and speed up clot formation. However, the granular form is awkward to apply in a windy environment, and the powder or bandage device is still subject to movement during extraction of the wounded patient, which can loosen the clot and cause leakage through the puncture to increase blood loss. Furthermore, the granular material is very exothermic, to the extent it can cause burns, and is difficult to combine with manual pressure because of the temperature generated. QuickClot™ has since been replaced with Combat Gauze™ (Z-Medica) which is a gauze impregnated with a kaolin substance which is not exothermic and does not have the disadvantages of a granular powder. It takes at least three to five minutes of manual pressure over the hemostatic agent before it is effective.

Even in a field hospital, bleeding from wounds can be problematic when faced with multiple penetration wounds. Penetrating wounds may not appear to bleed because the patient is in shock, but will often commence or resume bleeding upon resuscitation and return of systolic blood pressure. The surgeon often does not have enough time to close multiple wounds before bringing the patient to an operating room for urgent surgery.

Many wound closure devices are known in the art, however, may be improved upon in many different facets. There is a need in the art for a wound closure device which may be convenient to use, is relatively compact, and is effective in closing a wound under difficult situations which may arise in emergency situations, such as during warfare, terrorist attacks, accidents or during natural disasters.

SUMMARY OF THE INVENTION

The present invention relates to a wound closure device. The device rapidly re-approximates the skin edges by engaging the skin to seal the wound. The device is configured to open and close in a clam-shell configuration, and may be configured to be operated one-handed. In one embodiment, the device comprises needles which puncture the skin edges when the device is closed, and a pressure bar which applies pressure substantially perpendicular to the long axis of the wound. In one embodiment, the pressure bar comprises end closure members which are disposed substantially perpendicular to the pressure bar. The pressure is initially exerted manually by closing the device onto the skin surrounding the wound. The device may be maintained in a closed position by a biasing means, by a ratcheting mechanism, by friction or some other mechanical configuration.

Without restriction to a theory, the applicants believe that by closing the wound tightly between two opposing members, blood loss from the wound can be minimized even if there are significant wounds below the surface of the skin, if the wound is in a compressible zone. The patient may then be transported to a surgical facility with a minimized risk of bleeding out in the meantime. In one embodiment, the end closure members hem in the wound from the ends, further enhancing the closure of the wound.

Control of bleeding is achieved when pressure in or on the wound exceeds arterial or venous pressures. Packing of the wound with gauze or hemostatic agents prior to skin closure may be preferable for some wounds. Since the device seals off the skin from the outside it can also be used to prevent bowel evisceration out of a wound or to treat a sucking chest wound.

Therefore, in one aspect, the invention may comprise a wound closure device comprising:
(a) a first opposing member and a second opposing member engaged about a longitudinal axis, each pivotally moveable around the axis between a closed position and an open position relative to each other, and moveable longitudinally along the axis from a first position to a second position, each of the opposing members having a proximal edge adjacent the longitudinal axis and a distal edge, and an outer face and an inner face;
(b) a first ratchet on the first member, and a second ratchet on the second member, which engage each other to maintain the opposing members in the closed position, when the first and second members are in the first position, and which disengage when the first and second members are in the second position; and
(c) a plurality of needles disposed on the distal edges of the first and second members.

In one embodiment, each opposing member comprises an end closure member at each end, which is substantially perpendicular to the distal edge, and is aligned with an end closure member on the other opposing member.

In another aspect, the invention comprises a wound closure device comprising:
(a) a first opposing member and a second opposing member engaged about a longitudinal axis, each pivotally moveable around the axis between a closed position and an open position relative to each other, each of the opposing members having a proximal edge adjacent the longitudinal axis and a distal edge;

(b) skin penetrating means for anchoring the device;

(c) a pressure bar along each distal edge; and (d) releasable means for biasing or maintaining the device in the closed position.

BRIEF DESCRIPTION OF THE FIGURES

In the drawings, like elements are assigned like reference numerals. The drawings are not necessarily to scale, with the emphasis instead placed upon the principles of the present invention. Additionally, each of the embodiments depicted are but one of a number of possible arrangements utilizing the fundamental concepts of the present invention. The drawings are briefly described as follows.

DETAILED DESCRIPTION

The invention relates to a wound closure device. When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

In general terms, one embodiment of the wound closure device is configured in a clam-shell type configuration, with a first opposing member (4) and a second opposing member (6) pivotally attached to each other about a pin (2) which defines a longitudinal axis of rotation. Each of the opposing members having an outer face and inner face and two ends. In one embodiment, each opposing member approximates a bisected cylinder which has a proximal edge (5) and a distal edge (7). The longitudinal pivoting axis (2) is adjacent the proximal edge. The two bisected cylinder halves approximate a cylinder when in the closed position, where the two distal edges are proximal to each other. When the first and second members are pivoted to an open position, the two distal edges are spread apart.

While the first and second opposing members (4, 6) are illustrated herein to be half-cylinder sections in the embodiment illustrated, they may be approximated by interconnected curved arms or another equivalent configuration.

In one embodiment, each opposing member comprises an end closure member (8) at each end. Each end closure member (8) is substantially perpendicular to the distal edge, and is aligned with an end closure member on the other opposing member. Preferably, when the device is in a closed position, two opposing end closure members (8) abut each other, or come towards each other, in order to enclose or partially enclose the volume between the two opposing members at each end. In an alternative embodiment, the distal edges (7) may be curved so that the distance between the two distal edges (7) is reduced towards the ends when the device is in a closed position. Either configuration is intended to minimize leakage from the wound from the ends of the wound.

Without restriction to a theory, the applicants believe that by closing the wound tightly, between the two opposing members and between the end closure members, blood loss from the wound can be minimized even if there are significant wounds below the surface of the skin, in a compressible zone of the body. The patient may then be transported to a surgical facility with a minimized risk of bleeding out in the meantime.

Figure 8:
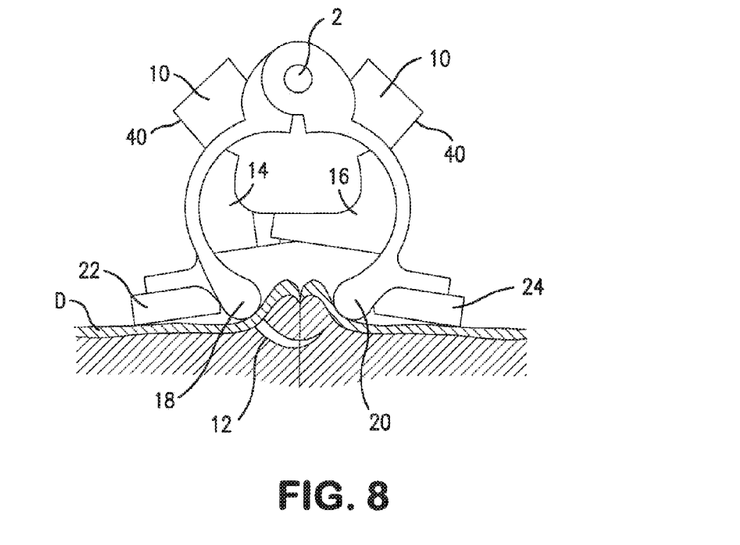
FIG. 8 is an end view of a clamp closed on a wound.

In one embodiment, the opposing members (4, 6) have needles (12) for piercing the skin on opposite sides of the wound. The needles have two primary functions. The first is to anchor the device into place when it is closed in place to seal a wound. If the device were to solely rely on frictional engagement with the skin, it might easily be knocked off. The second is to cause the skin and underlying tissue to bunch up between the opposing members, as is illustrated in FIG. 8. In one embodiment, the needles are long enough to penetrate the dermal layer (D) and extend into the underlying tissue. This action enhances the sealing action of the device.

In one embodiment, the needles (12) are alternately placed along the length of the opposing members such that the needles are interleaved. In one embodiment, the needles are curved such that the piercing of skin and closing of the device brings opposing edges of the wound up into the device, as is illustrated in FIG. 8. As a result, dermis to dermis contact along the length of the wound is promoted, which enhances the seal created by the device. As one skilled in the art will appreciate, the needles may have a radius of curvature similar to that of the first and second members.

In one embodiment, each of the opposing members (4, 6) has a pressure bar (18, 20) along the distal edge (7) of the member. Once the device is closed on a wound, the pressure bars (18, 20) exert relatively even pressure along the length of the wound to close the wound. The pressure bar may comprise frictional elements to help grip the skin, such as ridges (21) which run parallel to the distal edge.

In one embodiment, the pressure bar (18, 20) is configured to interact with or hide the needles of the opposing member in order to prevent exposing the needles when the device is being handled in the closed position. In one embodiment, the pressure bars may be lined with a resilient material (32) which envelops the needle tips, such as neoprene or another rubbery material. The resilient material may also aid in the application of pressure to the wound.

Figure 9:
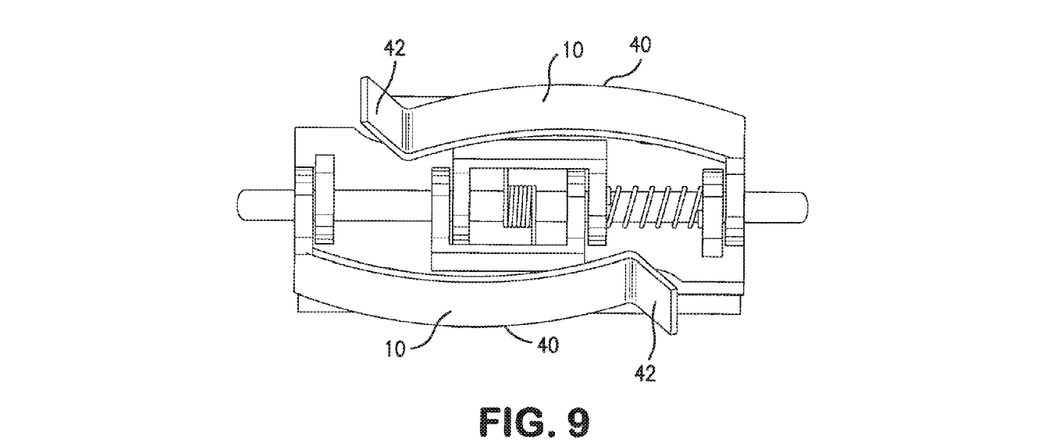
FIG. 9 is a top view of an alternative embodiment of the clamp.

In one embodiment, each of the opposing members (4, 6) has a grip (10) on the outer face. In one embodiment, the grips are raised concave surfaces placed near the pivot axis. The grips each provide a first gripping surface (40) which is substantially parallel to the longitudinal axis, which facilitates a one-handed opening motion. In one embodiment, the grips provide a second gripping surface (42) to push the first and second members apart along the longitudinal axis. The second gripping surface (42) may be substantially perpendicular to the longitudinal axis. Different grip configurations may provide suitable first and second gripping surfaces. In one embodiment, the grips may be optimized for such use, as is shown in FIG. 9.

The device is normally stored in a closed position, and is then opened by a user for use. In preferred embodiments, various mechanisms may be used to bias the device into an open position, but allow for storage in a closed position, and also allow for locking into a closed position when the device is in storage or in use.

Figure 7A:
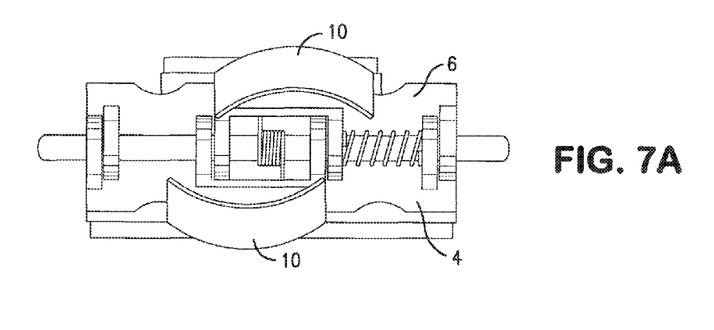
FIG. 7A is a top view of the clamp in the closed position with the ratchets engaged.
Figure 7B:
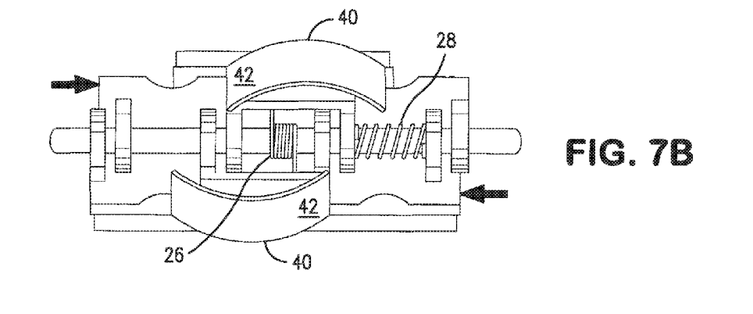
FIG. 7B is a top view of the clamp in the closed position but with the ratchets disengaged, allowing the device to be opened.

In one embodiment, the device may be biased towards its open position by a first spring (26) but is held in the closed position by cooperating ratchets (14, 16) disposed on the inner face of the first and second members. The ratchets (14, 16) are disengaged by moving the first member longitudinally away from the second member, as shown by the arrows in FIG. 7B, allowing the device to be opened. A second spring (28) places longitudinal pressure on the first and second members to keep the ratchets engaged.

Figure 1:
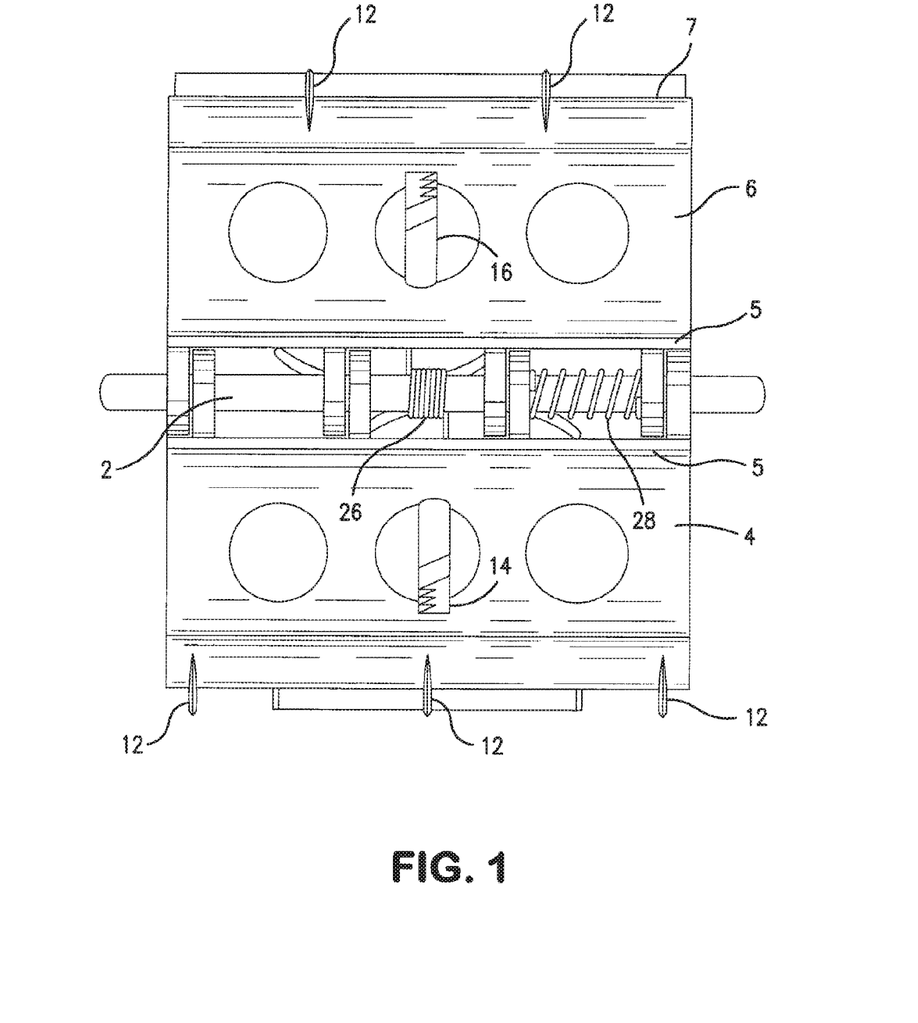
FIG. 1 is a bottom view of one embodiment of a clamp in the full open position.
Figure 2:
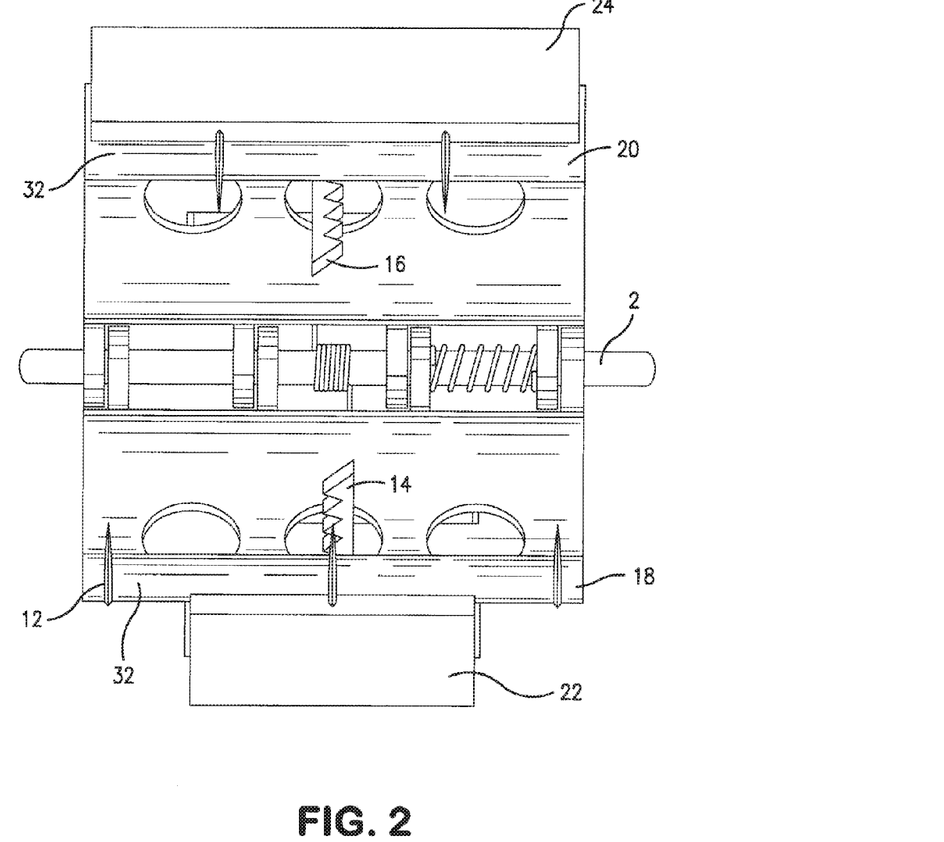
FIG. 2 is a bottom view of a clamp in a partially closed position.
Figure 3:
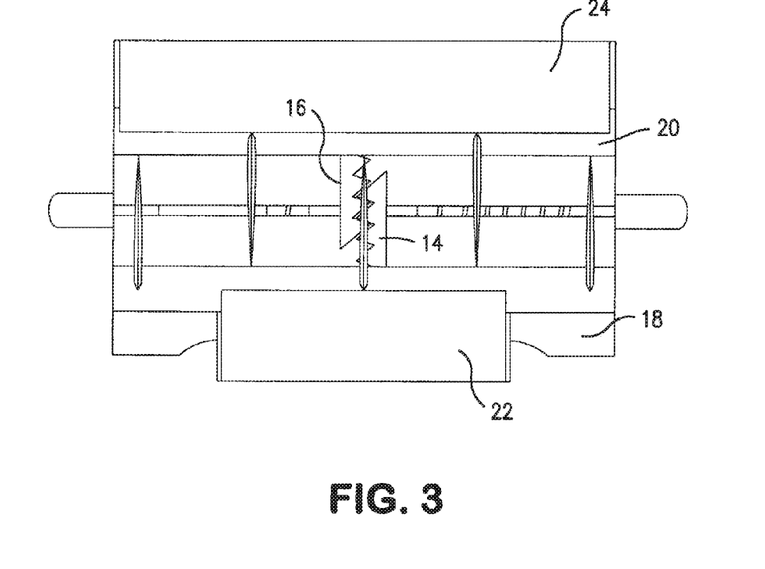
FIG. 3 is a bottom view of a clamp in a fully closed position.
Figure 4A:
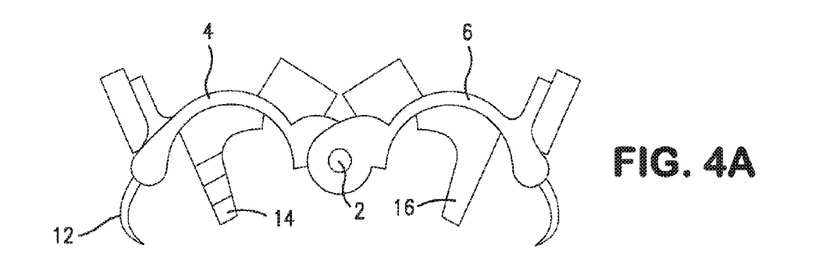
FIGS. 4A, 4B, 4C, 4D are end views of a clamp in an open and partially closed and closed position, respectively.
Figure 4B:
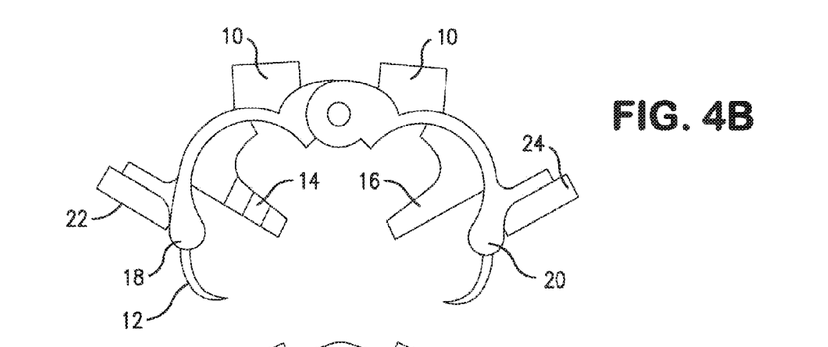
Figure 4C:
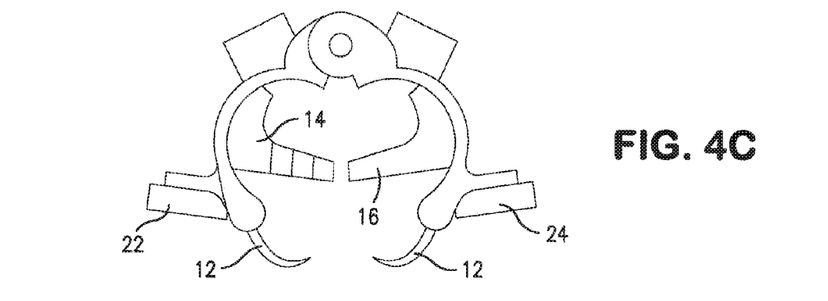
Figure 4D:
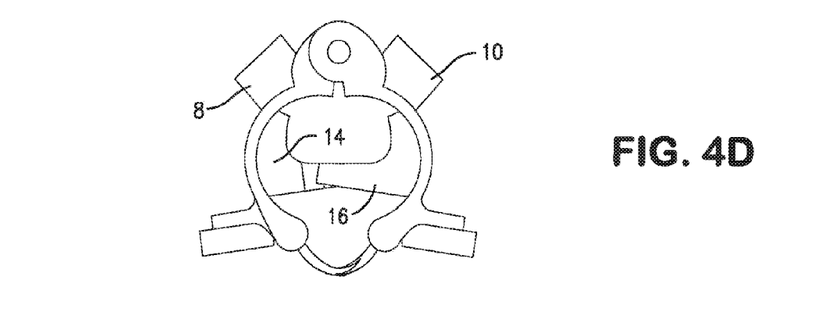
Figure 5:
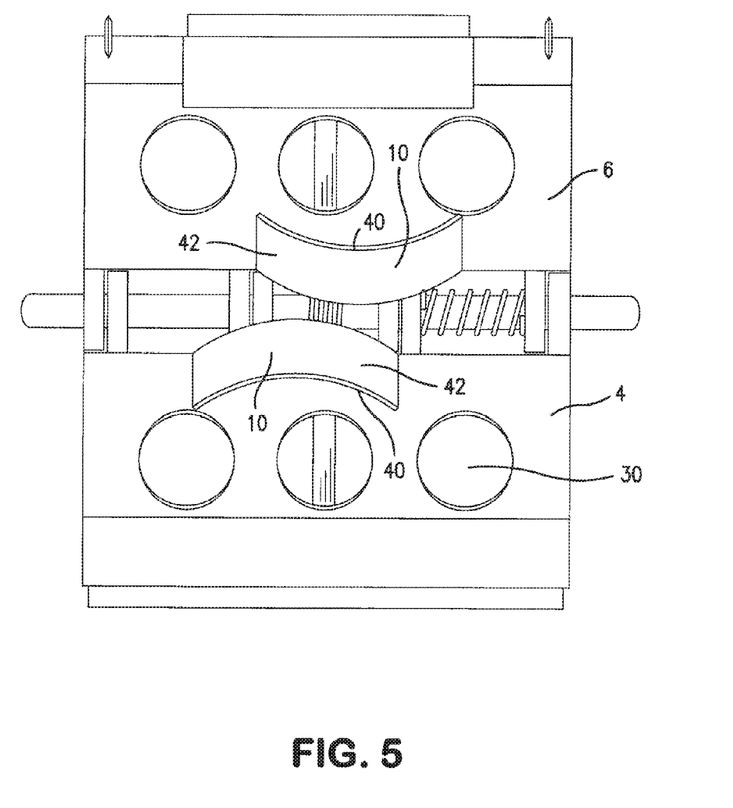
FIG. 5 is a top view of a clamp in a partially closed position.
Figure 6:
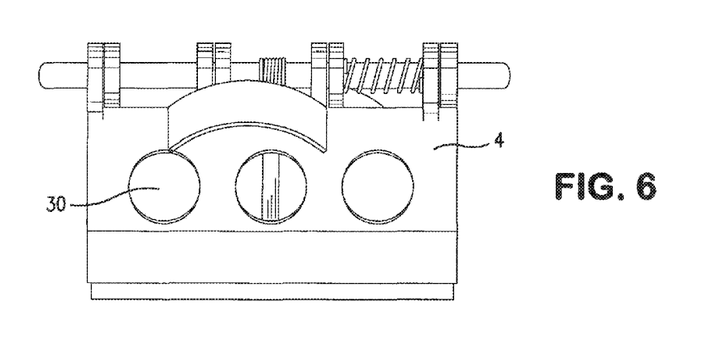
FIG. 6 is a side view of a clamp in a closed position.

A plurality of ratchet teeth on each opposing ratchet permits the user to control the closed position. In the fully closed position, the distal edges of the opposing members are adjacent each other, the opposing needles overlap, and all the ratchet teeth are engaged, as shown in FIG. 4D. The device may be partially closed, such as when placed on a wound, by engaging only the end teeth of the opposing ratchets.

Once the device is opened, it may be closed on the wound by forcing the two opposing members closed, against the pressure of the first spring (26), until the opposing ratchets engage each other.

In an alternative embodiment, the surfaces of the two opposing members which rotationally engage each other, about the longitudinal axis, may bear elements which frictionally engage each other. For example, one opposing member may comprise an outer cylindrical surface, while the other comprises an inner cylindrical surface. The two cylindrical surfaces bear against each other, and may provide sufficient friction to maintain the device in a closed position. Frictional elements such as raised ridges on the cylindrical bearing surfaces may provide additional friction.

Figure 10:
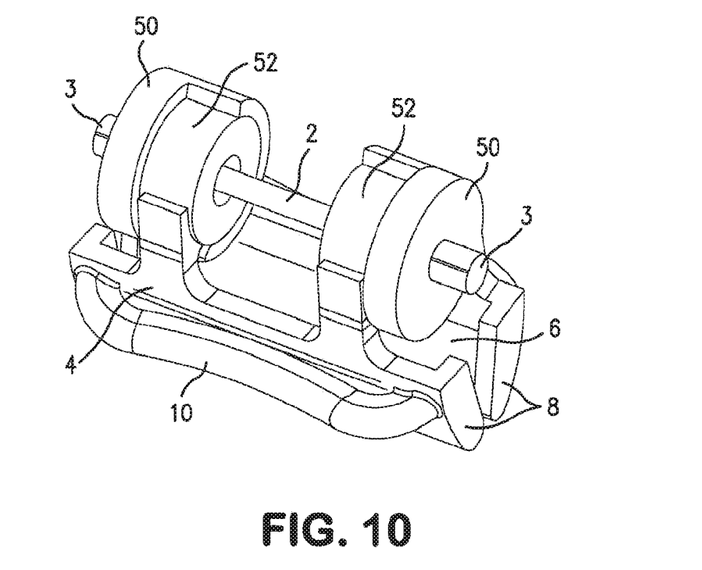
FIG. 10 is a view of a further alternative embodiment of the clamp.
Figure 11:
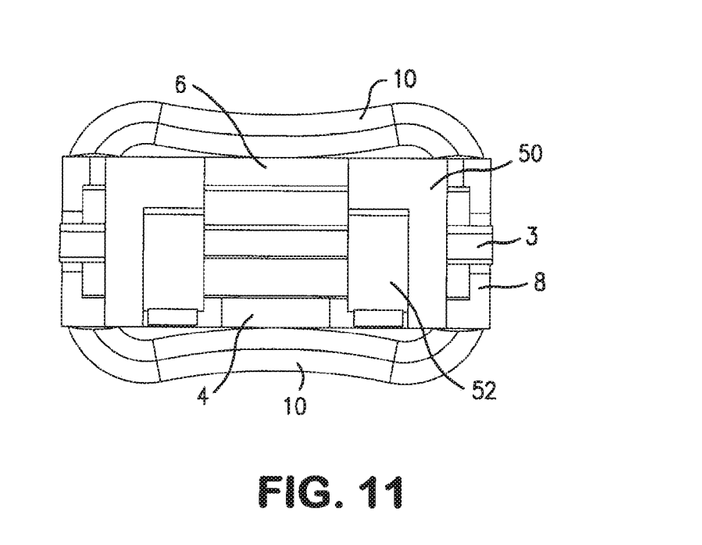
FIG. 11 is a top view of the embodiment of FIG. 10.
Figure 12:
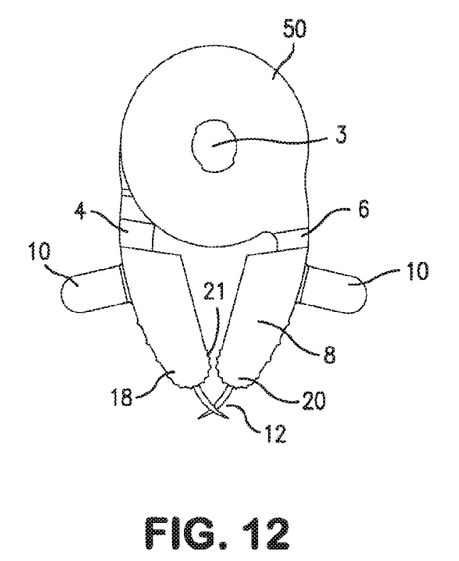
FIG. 12 is an end view of the embodiment of FIG. 10.
Figure 13:
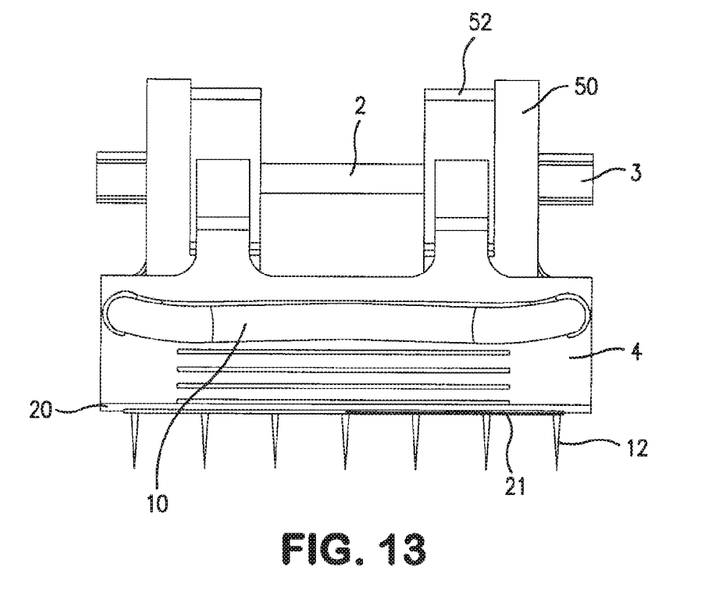
FIG. 13 is a side view of the embodiment of FIG. 10.
Figure 14:
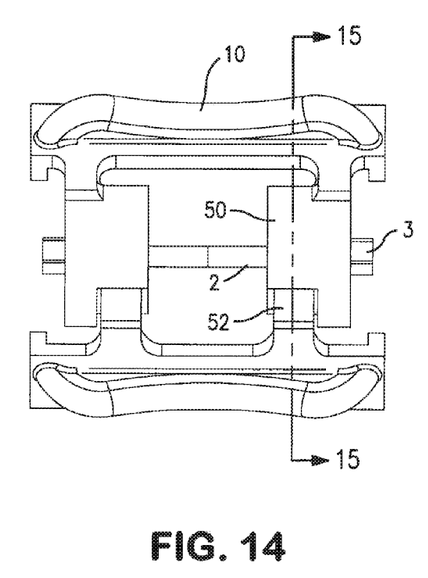
FIG. 14 is a top view of the embodiment of FIG. 10 in an open position.
Figure 15:
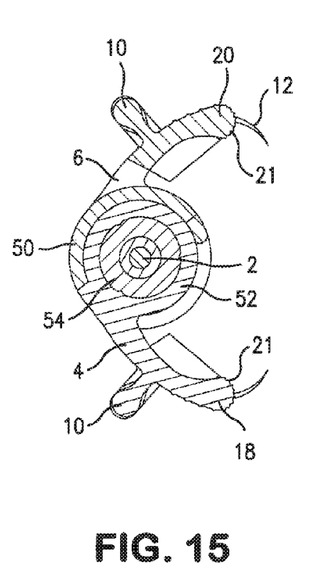
FIG. 15 is a cross-sectional view along line 15-15 in FIG. 14.

In another embodiment, the device comprises a releasable engagement mechanism comprising a one-way bearing. As shown in FIG. 10, the two opposing members (4, 6) rotationally engage each other about an axial pin (2) with a cylindrical bearing. The pin (2) is keyed at each end (3) so as to rotate with an outer cylinder (50) while being moveable in the axial direction. An inner cylinder (52) rotates within the outer cylinder (50). A one-way bearing (54) fits within and is affixed to the inner cylinder and is frictionally engages an engagement section of the pin (2) which passes through the bearing (54). The pin (2) comprises two telescoping sections which are biased outwards with an internal spring, and which can be overcome by pressing the two ends (3) inwards. The pin (2) also comprises a reduced diameter portion which is smaller than the engagement section and the inner diameter of the bearing (54). When the pin is in a relaxed state, the engagement section of the pin engages the inner diameter of the one-way bearing, which permits the device to rotate closed, but prevents rotation in the open direction. When the pin is compressed by squeezing the two ends (3), the pin slides laterally such that the reduced diameter portion is disposed within the one-way bearing, permitting free rotation in either direction.

In one embodiment, the cylinder and one-way bearing assemblies are provided at both ends of the device, which permits greater torque loads on the device in the closed position. It also permits slightly asymmetric application of the device on a wound, where the distal edges of the two opposing members are not exactly parallel. The torsional force acting on the one-way bearing at each end may be different.

Accordingly, a user can with one hand and one motion close the device about a wound, and the device will remain locked in a closed position. The device can be unlocked to release the device to its open position by a simple movement, again permitting one-handed use, if necessary or desired.

The scope of the invention includes alternative mechanical configurations which permit rotation of the two opposing members and a releasable locking or latching of the device into a closed position.

In one embodiment, each of the opposing members (4, 6) may have an optional stabilizing pad (22, 24) for balancing the device about a closed wound. Because of the mass of the device, it may have a tendency to sway when in position, closed on a wound. The stabilizing pads (22, 24) prevent or limit that swaying motion. In one embodiment, the stabilizing pads are extended along the length of the distal edge, approximately tangent to the cylinder formed by the closed members and parallel to the surface of the wound.

In one embodiment, each of the opposing members (4, 6) defines a number of openings (30), which allow the user to visualize the wound. The openings (30) may also allow access for medical or surgical instruments while the device is in use.

In one embodiment, the wound closure device is provided as a kit comprising a wound closure device in a sterile package, which may be opened with one hand. Therefore, it may be seen that a user may take the sterile package, open it and remove the device which is stored in its closed position, open it with one hand, place it on a wound, and close it, all with one hand and in very little time.

The invention claimed is:

1. A wound closure device comprising:
 (a) a first opposing member and a second opposing member engaged about a longitudinal axis, each pivotally moveable around the axis between a closed position and an open position relative to each other, each of the opposing members having a proximal edge adjacent the longitudinal axis and a distal edge;
 (b) skin penetrating means for anchoring the device, wherein the skin penetrating means comprises a plurality of needles;
 (c) a pressure bar along each distal edge; and
 (d) releasable locking means for biasing or maintaining the device in the closed position,
 wherein the releasable locking means comprises a one-way cylindrical bearing disposed between the first and second opposing members, and a longitudinal pin disposed within the bearing, wherein the one-way bearing rotates with one opposing member, and the pin rotates with the other opposing member, and wherein the pin comprises an engagement section which engages the bearing to rotate freely in one direction but not the other direction, and a reduced diameter section where the pin freely rotates in either direction, and the pin is moveable longitudinally to slide the reduced diameter section into and out of the bearing.

2. The device of claim 1 wherein each opposing member comprises an end closure member substantially perpendicular to the distal edge and aligned with an opposing end closure member.

3. The device of claim 1 wherein the needles are of sufficient length to penetrate the skin and pierce underlying tissue.

4. The device of claim 3 wherein the needles are curved, with a radius of curvature substantially similar to a radius of curvature of the opposing members.

5. The device of claim 1 wherein the needles are curved, with a radius of curvature substantially similar to a radius of curvature of the opposing members.

6. The device of claim 1 wherein the two opposing members frictionally engage each other to remain in a closed position.

7. The device of claim 6 wherein the frictional engagement is enhanced by a plurality of longitudinal ridges on one or both of the opposing member bearing surfaces.

8. The device of claim 1 wherein the device comprises two releasable locking means, one at either end of the device.

* * * * *